(12) United States Patent
Birnkrant (10) Patent No.: US 8,651,107 B2
(45) Date of Patent: Feb. 18, 2014

(54) MANUAL LUNG VENTILATION DEVICE

(75) Inventor: David J. Birnkrant, Moreland Hills, OH (US)

(73) Assignee: The Metrohealth System, Cleveland, OH (US)

( * ) Notice: Subject to any disclaimer, the term of this patent is extended or adjusted under 35 U.S.C. 154(b) by 1453 days.

(21) Appl. No.: 11/874,982

(22) Filed: Oct. 19, 2007

(65) Prior Publication Data

US 2008/0092895 A1  Apr. 24, 2008

Related U.S. Application Data

(60) Provisional application No. 60/853,412, filed on Oct. 20, 2006.

(51) Int. Cl.
*A61M 16/08* (2006.01)
*A61M 16/06* (2006.01)
*A61M 16/00* (2006.01)

(52) U.S. Cl.
USPC ............ 128/207.11; 128/206.27; 128/206.21; 128/205.13; 128/202.28; 128/200.24

(58) Field of Classification Search
USPC ............. 128/200.24, 201.22, 201.23, 201.29, 128/205.13, 206.21, 206.27, 207.11, 128/207.13, 207.18
See application file for complete search history.

(56) References Cited

U.S. PATENT DOCUMENTS

| 196,206 A | 10/1877 | Emery |
|---|---|---|
| 1,044,031 A | 11/1912 | Drager |
| 1,343,486 A | 6/1920 | Stolle |
| 1,358,893 A | 11/1920 | Stolle |
| 2,199,690 A * | 5/1940 | Bullard .................... 128/207.11 |
| 2,914,064 A | 11/1959 | Sandelowsky |
| 3,342,177 A | 9/1967 | Clementz |
| 3,426,794 A | 2/1969 | Freytag |
| 3,682,166 A | 8/1972 | Jacobs |
| 3,766,914 A | 10/1973 | Jacobs |
| 3,796,216 A * | 3/1974 | Schwarz .................. 128/205.13 |
| 3,882,860 A * | 5/1975 | Frimberger .............. 128/202.16 |

(Continued)

FOREIGN PATENT DOCUMENTS

| CA | 2230622 | 9/1998 |
|---|---|---|
| GB | 23021 | 0/1914 |

(Continued)

OTHER PUBLICATIONS

Response from European Application No. 07844434.6 dated Mar. 3, 2010.

(Continued)

*Primary Examiner* — Annette Dixon
(74) *Attorney, Agent, or Firm* — Fay Sharpe LLP; Richard M. Klein (57) ABSTRACT

A manual lung ventilation device and method suitable for acute manual respiratory resuscitation and lung ventilation of a person are disclosed. The manual lung ventilation device includes a nasal interface in fluid communication with a flexible chamber. The nasal interface being held in the proper position on the person by a headgear and at least one securing device adapted to connect the nasal interface to the headgear. The device may be formed as a single component to allow an operator to rapidly position the device on the person to be ventilated and operate the device with one hand.

23 Claims, 7 Drawing Sheets

(56) References Cited

U.S. PATENT DOCUMENTS

| | | | | |
|---|---|---|---|---|
| 4,077,404 A * | 3/1978 | Elam | | 128/204.28 |
| 4,193,406 A | 3/1980 | Jinotti | | |
| 4,367,735 A * | 1/1983 | Dali | | 128/207.18 |
| 4,374,521 A * | 2/1983 | Nelson et al. | | 128/205.13 |
| 4,532,923 A * | 8/1985 | Flynn | | 128/205.13 |
| 4,870,962 A * | 10/1989 | Sitnik | | 128/205.13 |
| 5,109,839 A | 5/1992 | Blasdell et al. | | |
| 5,211,171 A | 5/1993 | Choromokos | | |
| 5,301,667 A * | 4/1994 | McGrail et al. | | 128/205.14 |
| 5,311,862 A | 5/1994 | Blasdell et al. | | |
| 5,345,930 A | 9/1994 | Cardinal et al. | | |
| 5,404,873 A * | 4/1995 | Leagre et al. | | 128/204.18 |
| 5,419,317 A | 5/1995 | Blasdell et al. | | |
| 5,533,506 A | 7/1996 | Wood | | |
| 5,540,221 A * | 7/1996 | Kaigler et al. | | 128/205.13 |
| 5,542,128 A * | 8/1996 | Lomas | | 2/173 |
| 5,546,934 A * | 8/1996 | Kaigler et al. | | 128/205.13 |
| 5,711,295 A * | 1/1998 | Harris, II | | 128/202.28 |
| 5,791,340 A | 8/1998 | Schleufe et al. | | |
| 5,850,835 A | 12/1998 | Takaki et al. | | |
| 6,119,692 A * | 9/2000 | Byram | | 128/206.27 |
| 6,176,235 B1 | 1/2001 | Benarrouch et al. | | |
| 6,209,540 B1 | 4/2001 | Sugiura et al. | | |
| 6,427,691 B1 | 8/2002 | Jinotti | | |
| 6,539,941 B2 * | 4/2003 | Haubeil | | 128/205.13 |
| 6,543,446 B1 | 4/2003 | Christopher | | |
| 6,637,434 B2 | 10/2003 | Noble | | |
| 6,776,160 B2 * | 8/2004 | Wang | | 128/205.13 |
| 6,789,538 B2 | 9/2004 | Wright et al. | | |
| 6,789,540 B1 | 9/2004 | Lin | | |
| 6,860,265 B1 | 3/2005 | Emerson | | |
| 6,929,007 B2 | 8/2005 | Emerson | | |
| 7,032,596 B2 | 4/2006 | Thompson et al. | | |
| 7,096,866 B2 | 8/2006 | Be'eri et al. | | |
| 7,219,670 B2 | 5/2007 | Jones, Jr. et al. | | |
| 7,225,811 B2 * | 6/2007 | Ruiz et al. | | 128/207.11 |
| D597,659 S | 8/2009 | Chandran et al. | | |
| 7,806,118 B2 * | 10/2010 | Thompson et al. | | 128/205.13 |
| 2002/0069875 A1 * | 6/2002 | Kuo | | 128/202.28 |
| 2003/0024533 A1 | 2/2003 | Sniadach | | |
| 2003/0051731 A1 | 3/2003 | Be'eri et al. | | |
| 2003/0075182 A1 | 4/2003 | Heidmann et al. | | |
| 2003/0154980 A1 | 8/2003 | Berthon-Jones et al. | | |
| 2005/0139220 A1 | 6/2005 | Christopher | | |
| 2005/0217675 A1 | 10/2005 | Thompson et al. | | |
| 2005/0263157 A1 | 12/2005 | Olsen | | |
| 2006/0060199 A1 * | 3/2006 | Lampotang et al. | | 128/205.13 |
| 2006/0124131 A1 | 6/2006 | Chandran et al. | | |
| 2006/0130845 A1 | 6/2006 | Schegerin | | |
| 2006/0191536 A1 * | 8/2006 | Kroupa et al. | | 128/205.13 |
| 2006/0249158 A1 | 11/2006 | Dhuper et al. | | |
| 2007/0017522 A1 | 1/2007 | Be'eri et al. | | |
| 2007/0017523 A1 | 1/2007 | Be'eri et al. | | |
| 2007/0089740 A1 | 4/2007 | Baumert et al. | | |
| 2007/0186928 A1 | 8/2007 | Be'eri | | |
| 2007/0199566 A1 | 8/2007 | Be'eri | | |
| 2007/0272247 A1 | 11/2007 | Porat | | |
| 2007/0272248 A1 | 11/2007 | Lin | | |
| 2007/0272249 A1 | 11/2007 | Chandran et al. | | |
| 2008/0015475 A1 * | 1/2008 | Lau et al. | | 601/41 |
| 2008/0087285 A1 * | 4/2008 | Kuo | | 128/205.13 |
| 2009/0071482 A1 * | 3/2009 | Huddlestone | | 128/205.13 |
| 2009/0159084 A1 | 6/2009 | Sher et al. | | |

FOREIGN PATENT DOCUMENTS

| | | |
|---|---|---|
| JP | 05096007 A | 4/1993 |
| JP | 10165505 A | 6/1998 |
| NZ | 233225 | 4/1990 |
| WO | 2004/108199 | 12/2004 |
| WO | 2007/054829 | 5/2007 |
| WO | 2008/051816 | 5/2008 |

OTHER PUBLICATIONS

Printout from http://www.nagelnetwork.com/mouth.htm, 4 pgs., Mouthpieces, Flow Sensors & Noseclips, printed Nov. 11, 2009.

Four pages, Pediatric Advanced Life Support Textbook from the American Heart Association including pp. 4-10 and 4-11, dated 1994.

Four page web printout from http://www.ambu.com/RespiratoryCare/Respiratory_Care.aspx? GID=GROUP51&Product . . . , date unknown, printed on Jan. 30, 2009, Ambu Mark IV—Reusable Resuscitator.

One page printout from http://www.laerdaltraining.com/lsr/, Laerdal, date unknown, printed Apr. 16, 2009.

Open Lung Approach (OLA) Using Conventional Mechanical Ventilation (CMV) or High Frequency Oscillation (HFO) Improves Oxygenation and Compliance in Ards Better Than the Ardsnet Protocol, Maria Paula Caramez MD, Mohamed Helmy MD, Eriko Miyoshi MD, R. Scott Harris MD, Atual Malhotra MD, and Robert M. Kacmarek PHD, RRT, Abstract Published Nov. 2006, Respiratory Care, vol. 51 No. 11, presented at Dec. 2006 Convention.

Noninvasive Ventilation During Gastrostomy Tube Placement in Patients with Severe Duchenne Muscular Dystropy, D.J. Birnkrant, MD, R.D. Ferguson, MD, J.E. Martin RRT and G.J. Gordon MD, Pediatric Pulmonology 41: pp. 118-193 dated Feb. 2006.

Use of the Laryngeal Mask Airway in Patients with Severe Muscular Dystrophy Who Require Sedation or Anesthesia, David J. Birnkrant, MD, Kasia M. Petelenz, MD, Roy D. Ferguson, MD, James E. Martin, RRT, and Gregory J. Gordon, MD., Pediatric Pulmonology 41, pp. 1007-1081, published Nov. 2006.

International Search Report and Written Opinion for PCT Application No. PCT/US2007/081869, mailed Nov. 13, 2008, 19 pages.

International Search Report and Written Opinion from PCT/US09/64746 dated Jan. 20, 2010.

Communication issued in European Patent Application Serial No. 07844434.6 dated Aug. 27, 2009.

Office Action for Chinese Patent Application No. 200780038700.8, dated May 12, 2011.

* cited by examiner

MANUAL LUNG VENTILATION DEVICE

RELATED APPLICATIONS

This application claims priority to, and any other benefit from, U.S. Provisional Patent Application Ser. No. 60/853,412 filed Oct. 20, 2006, for MANUAL LUNG VENTILATION DEVICE, the entire disclosure of which is fully incorporated herein by reference.

BACKGROUND

Rescue breathing or "mouth-to-mouth resuscitation" is a specific first aid protocol which refers to the delivery of air from a person (the rescuer) into a person who is having difficulty breathing or has stopped breathing altogether. A person who is capable will use their own breath at prescribed intervals to push oxygen into the lungs of the person. Rescue breathing, however, can be difficult to perform properly and requires the rescuer be specially trained in administering it. In addition, because the rescuer and the person are in mouth-to-mouth contact, there may be concerns regarding rescuer safety and contracting infectious diseases. Another method by which a person may receive manual lung ventilation involves use of a device consisting of a ventilation bag attached to a full face mask. Special skills are needed to apply this device properly and to use it effectively, relegating it to the almost exclusive use of medical professionals. Therefore, a simple and easy-to-use device and method suitable for acute manual respiratory resuscitation and lung ventilation are desirable.

SUMMARY

The present application discloses a manual lung ventilation device and method. In particular the application discloses a manual lung ventilation device suitable for acute manual respiratory resuscitation and lung ventilation.

In accordance with one embodiment, a device is provided for manually resuscitating and/or ventilating the lungs of a person via the person's nasal passages. The device may include a nasal only interface in fluid communication with a flexible chamber.

In accordance with another embodiment, a device is provided that may quickly and easily be correctly positioned on a person for resuscitating or ventilating the lungs of the person. The device may include a nasal interface in fluid communication with a flexible chamber and attached to a headgear. The nasal interface, flexible chamber, and headgear are attached as a single physical and functional unit or assembly such that when the headgear is placed on a person, the nasal interface is, in general, correctly positioned onto the person with little adjustment needed. Furthermore, the device secures the nasal interface in the correct position such that a person operating the device may manually ventilate the lungs using just one hand. In one embodiment, the nasal interface, the flexible chamber, and the headgear are attached in a permanent manner to form a single unit. In another embodiment the single unit is adjustably attached to a headgear such that the unit and headgear are not readily separable without some disassembly of the device.

Further aspects and concepts will become apparent to those skilled in the art after considering the following description and appended claims in conjunction with the accompanying drawings.

BRIEF DESCRIPTION OF THE DRAWINGS

In the accompanying drawings, which are incorporated in and constitute a part of the specification, embodiments of the invention are illustrated, which, together with a general description of the invention given above, and the detailed description given below, serve to exemplify embodiments of the invention.

DETAILED DESCRIPTION

The present application discloses a manual lung ventilation device. While the exemplary embodiments illustrated and described herein are presented in the context of a device configured to provide acute manual respiratory resuscitation and lung ventilation, which includes a self-inflating bag and a nasal mask that may be secured to a person by a skull cap, those skilled in the art will readily appreciate that the present invention may be used and configured in other ways. For example, the device may be used in applications beyond acute manual respiratory resuscitation, such as for example, providing ventilation for persons under anesthesia or sedation. In addition, the device may be configured to include other ways of securing the nasal mask to the person and of forcing air into the person's lungs. For example, any suitable headgear that can be quickly placed on the person to secure the nasal mask in place may be used. Furthermore, instead of a self-inflating bag, an air chamber that is inflated by a pressure source, such as a tank of pressured oxygen, may be used. Still further, the nasal interface may be other than a mask. Any device capable of interfacing with a person's nose to allow pressurized air or oxygen to be delivered through the nose to the person's lungs may be used.

While various aspects and concepts of the invention are described and illustrated herein as embodied in combination in the exemplary embodiments, these various aspects and concepts may be realized in many alternative embodiments, either individually or in various combinations and sub-combinations thereof. Unless expressly excluded herein all such combinations and sub-combinations are intended to be within the scope of the present invention. Still further, while various alternative embodiments as to the various aspects and features of the invention, such as alternative materials, structures, configurations, methods, devices, and so on may be described herein, such descriptions are not intended to be a complete or exhaustive list of available alternative embodiments, whether presently known or identified herein as conventional or standard or later developed. Those skilled in the art may readily adopt one or more of the aspects, concepts or features of the invention into additional embodiments within the scope of the present invention even if such embodiments are not expressly disclosed herein. Additionally, even though some features, concepts or aspects of the invention may be described herein as being a preferred arrangement or method, such description is not intended to suggest that such feature is required or necessary unless expressly so stated. Still further, exemplary or representative values and ranges may be included to assist in understanding the present invention however, such values and ranges are not to be construed in a limiting sense and are intended to be critical values or ranges only if so expressly stated.

Figure 1:
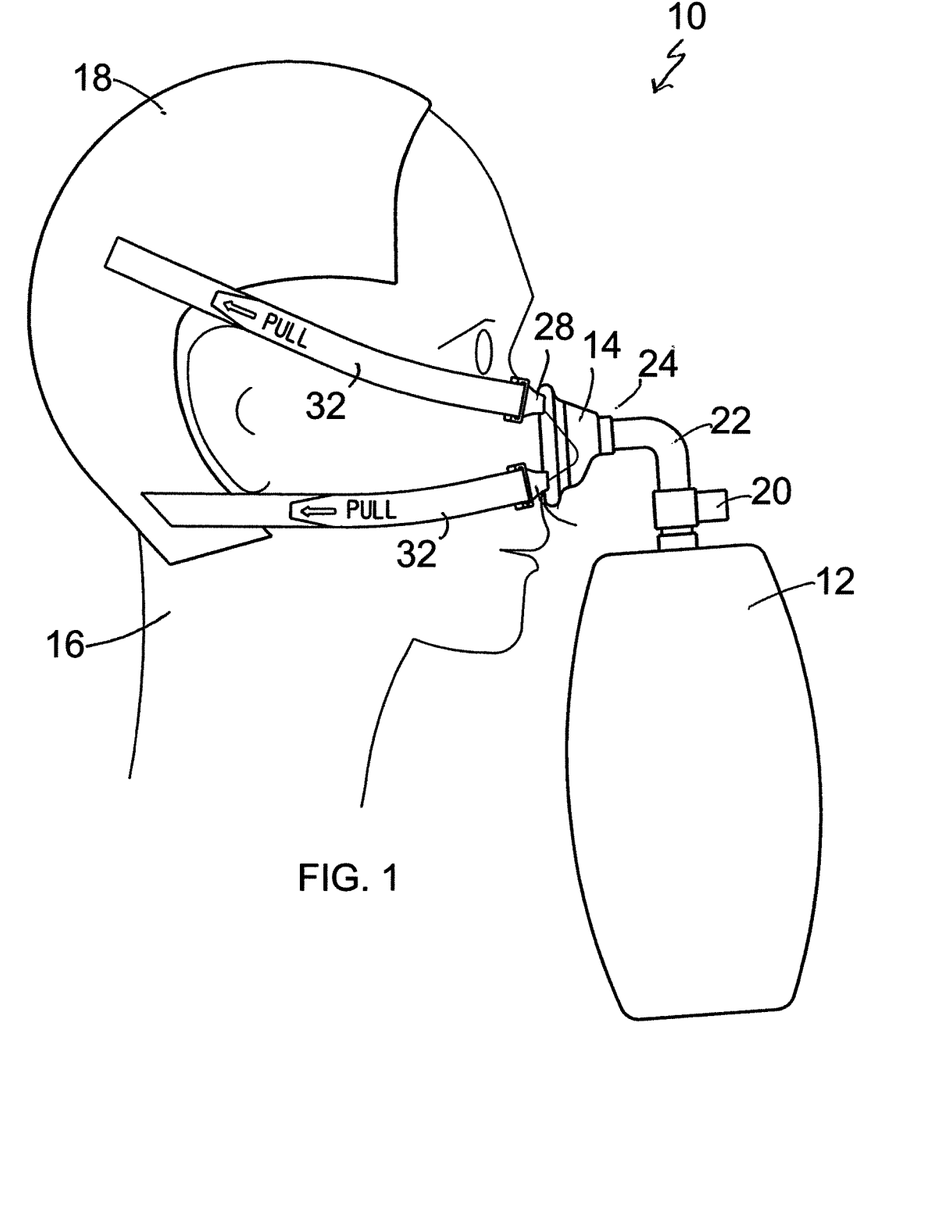
FIG. 1 is a side view of an exemplary embodiment of a manual lung ventilation device arranged on a person.
Figure 2:
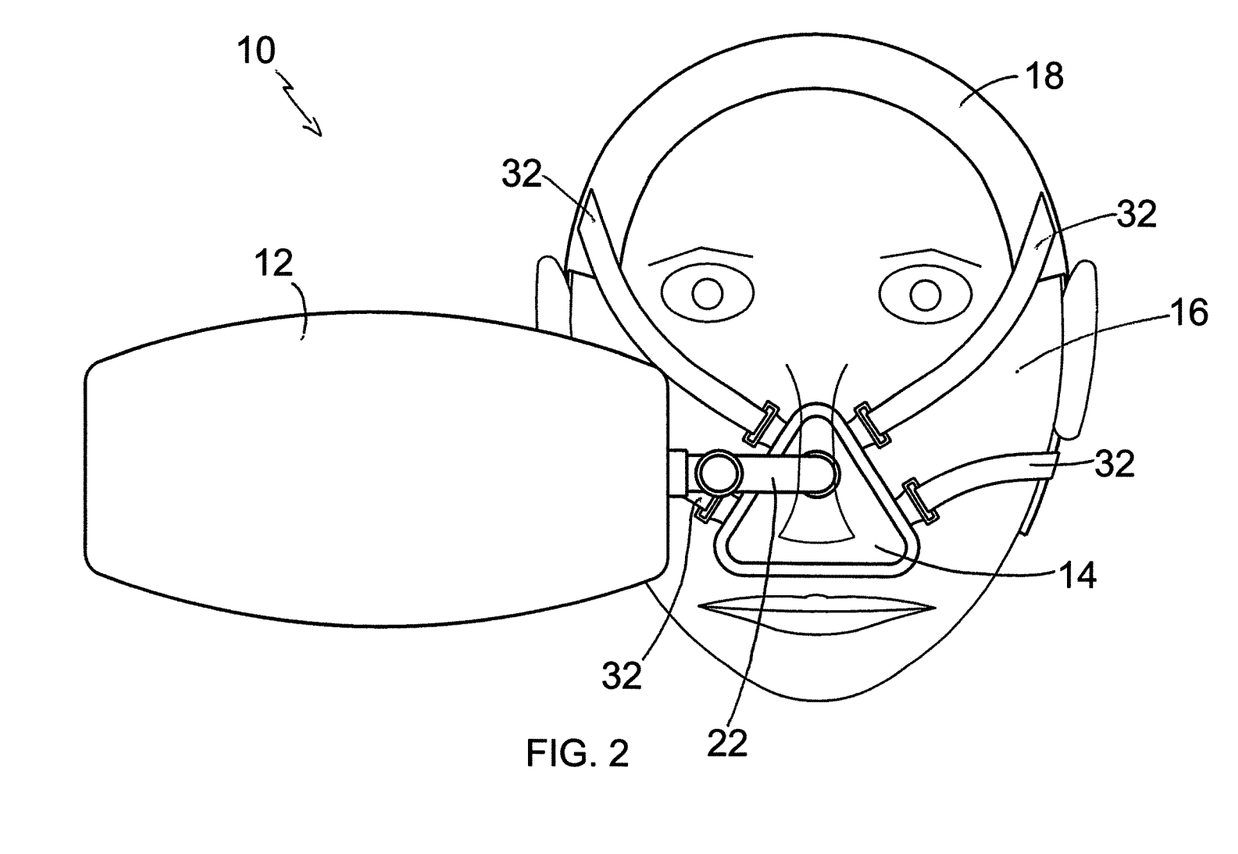
FIG. 2 is a front view of the manual lung ventilation device of FIG. 1.

FIGS. 1 and 2 illustrate an exemplary embodiment of a ventilation device 10 for resuscitation and lung ventilation. The device 10 includes a squeezable or flexible chamber or bag 12 in fluid communication with a nasal interface 14, such as for example a nasal mask. The terms "nasal interface" and "nasal mask", when used in this application, refer to an interface or mask adapted to transfer air to only the nasal passages of a person and not to the mouth of a person.

The nasal interface 14 is adapted to be held or secured in place on the face of a person 16 by a headgear 18. Compressing or squeezing the chamber 12 forces air through the nasal interface 14 and into the nasal passages of a person 16 to inflate and ventilate the person's lungs. The flexible chamber 12 is illustrated in FIG. 1 as extending generally parallel to a person 16 along the person's body. The flexible chamber 12, however, may be arranged, in relation to the person 16 and the nasal interface 14, in any convenient manner for operation of the device 10. For example, in FIG. 2, the flexible chamber 12 extends generally perpendicular to the person's body.

The device 10 is suitable for use in a wide variety of applications. For example, the device 10 may be used for on-site resuscitation for people who have experienced respiratory arrest as an alternative to mouth-to-mouth resuscitation. The device 10 may also be used in the home as an alternative to mechanical ventilation. For example, the device 10 may be used as a temporary ventilation device for people with chronic respiratory failure whose home mechanical non-invasive (nasal) ventilators fail due to malfunction or during a power outage, or when such persons are transferred between locations and attachment to the powered ventilator is impractical (e.g., when they are taking a bath, transferring to a wheelchair, or to a vehicle). Furthermore, the device 10 may be used in healthcare facilities or by emergency medical personnel as a prefabricated "kit" for rapid application of either manual resuscitation or to provide assisted ventilation, replacing manual bag-valve-full face mask ventilation, in a variety of healthcare delivery venues such as but not limited to: the operating room, the ward, the Emergency Department, the Intensive Care Unit (ICU), Critical Care Unit (CCU), or for use by emergency medical personnel in the community, etc. The device may be used by persons with chronic hypoventilation and shallow breathing, to provide sessions of deep breathing, for the purpose of preserving chest wall and lung compliance or suppleness, and to avoid and treat atelectasis or loss of lung volume. Still further, the device may be used to deliver assisted breathing to persons in respiratory distress, applied, for example, by emergency medical personnel in the field, or used for similar purposes in the hospital or other venues. In different embodiments, the device and its components (including the nasal interface, headgear, and flexible chamber) can be produced in any size, thereby making the device suitable for use with persons of any size or age, from neonates to adults.

The device described in this application embodies a new application of nasal ventilation, namely a method of manual, hand-powered ventilation for use primarily in acute medical settings, such as to provide resuscitation to people who have experienced respiratory arrest in the field or in the hospital, to provide respiratory support in the hospital for persons undergoing anesthesia or sedation, and to provide respiratory support in the home for people who require chronic ventilation, when those people travel between venues, when their ventilators malfunction, or during power outages. The device facilitates easy, rapid and effective placement on a person and allows one-handed operation. The design elements which permit rapid, effective person placement include the intimate connection of the headgear, the nasal mask, and the flexible chamber, which comprise a single unit; thus, when the headgear is placed on the person, the nasal mask easily falls into proper position, and lung ventilation can be initiated immediately by compressing the flexible chamber.

The flexible chamber 12 may be configured in a variety of ways. Any structure that can be inflated and then squeezed or compressed to force air from the structure can be used. In the depicted embodiment, the flexible chamber 12 is a self-inflating bag. The bag 12 is constructed of a resilient material, such as for example rubber or plastic polymer, such that when the bag is squeezed or compressed, it wants to return to its normal shape once released. On returning to its normal shape, air may be drawn into the bag 12 via a valve mechanism 20, such as for example a shuttle valve. In another embodiment, the flexible chamber 12 is not self-inflating but is instead attached to a source of pressurized gas, such as air or oxygen. When the chamber 12 is squeezed and released, the pressurized gas refills and expands the chamber.

The bag 12 is in fluid communication with the nasal interface 14. In the depicted embodiment, the bag 12 and the nasal interface 14 are connected by a conduit section 22. The conduit section 22 may be, but not necessarily be, permanently attached to or integrally formed with the nasal interface 14 to reduce the likelihood that the conduit section 22 and the nasal interface 14 may detach during installation or use of the device 10. For example, the nasal interface 14 and the conduit section 22 may be formed from an injection moldable plastic with the interface and conduit formed as a single molded piece. The interface 14 and conduit section 22, however, may be formed with any suitable material and by any suitable method.

In addition, the bag 12 may be, but not necessarily be, fixably attached to the conduit section 22 by any suitable means, such as for example, clamps, fasteners, adhesives, or other suitable methods. Thus, in one embodiment, the device 10 may have a single unit configuration that permanently connects the bag 12 to the nasal interface 14 so that the single unit remains connected during the process of resuscitation and/or lung ventilation and can be quickly installed upon a person 16.

Figure 3:
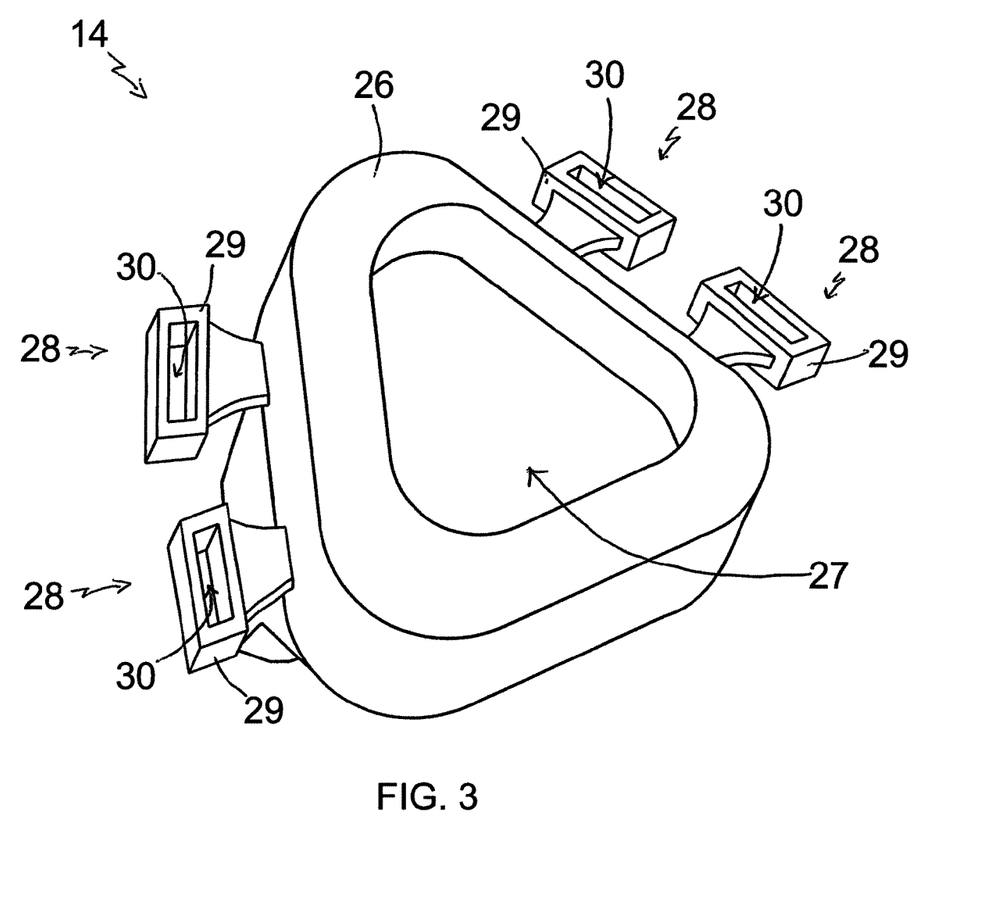
FIG. 3 is an illustration of an exemplary embodiment of a nasal mask of the device of FIG. 1.

Referring to FIG. 3, the nasal interface 14 may be configured in a variety of ways. Any device that allows a gas, such as air or oxygen, to be delivered under pressure to a person's lungs through the nasal passages of the person 16 may be used. In the depicted embodiment, the nasal interface 14 is realized as a nasal mask. The nasal mask 14 is generally cup-shaped and configured to fit over the nose of a person 16, but not over the person's mouth as with a full face mask, which fits over both the nose and mouth.

The mask 14 includes an inlet 24 for receiving air from the flexible chamber 12 and an edge 26 surrounding an outlet 27. The edge 26 is configured to engage the face of the person 16 and provide a seal such that air delivered to the mask 14 flows into the nasal passages of the person. To facilitate sealing, a portion of the mask including the edge 26 may include a seal element, such as but not limited to an elastomer, foam, or other resilient material. The mask 14 may also include one or more attachment portions 28 for attaching to the headgear 18. In the depicted embodiment, the attachment portions 28 extend from the sides of the mask and include a body 29 defining an opening 30 for attaching to the headgear 18.

Figure 4:
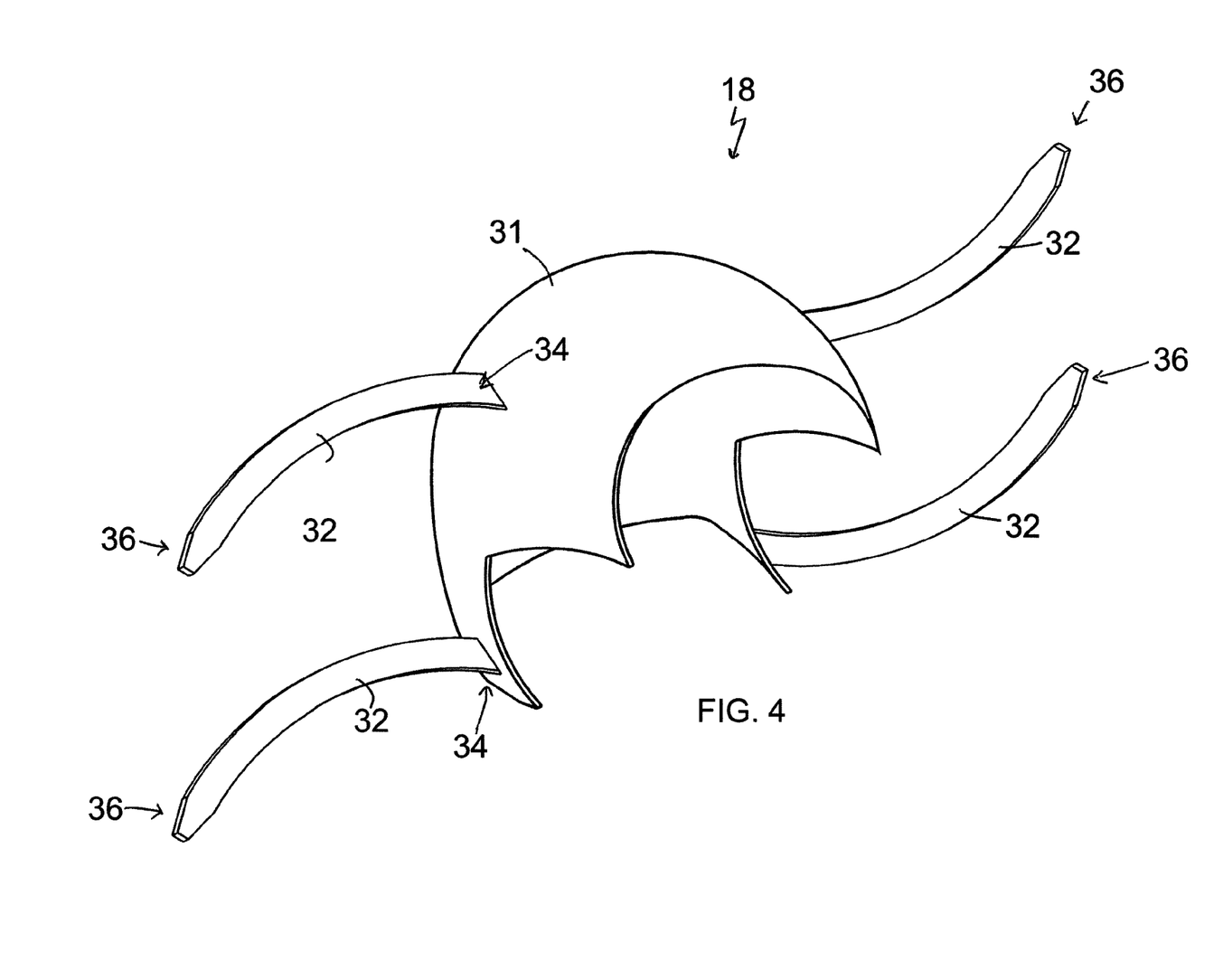
FIG. 4 is an illustration of an exemplary embodiment of a headgear of the device of FIG. 1.

Referring to FIG. 4, the headgear 18 may be configured in a variety of ways. Any device that secures the nasal interface 14 in place on the person 16 may be used. In the depicted embodiment, the headgear 18 is realized as a skull cap. The cap 18 includes a head-conforming portion 31 and one or more securing devices 32 for attaching to the interface 14, such as for example, straps. In the depicted embodiment, four straps are included, though any number of straps may be used. Each strap 32 has a first end 34 fixably attached to the head-conforming portion 31 and a second or distal end 36 adapted to fit through the opening 30 on the corresponding attachment portion 28 on the nasal interface 14. Once through the opening 30, the strap 32 may be pulled back toward the head conforming portion 31 to tighten the mask 14 to the person's face. A Velcro® brand type of hook and loop fastener, for example, may be included on the straps 32 and/or head conforming portion 31 to secure the second end 36 after tightening. Thus, the attachment portions 28 and the securing devices 32 cooperate to secure and hold the nasal interface 14 in the proper position. The number, arrangement and configuration of the securing devices and attachment portions may vary between different embodiments of the device. Any suitable cooperating structure capable of quickly securing and holding the nasal interface in the proper position may be used. For example, a variety of adjustable strap configurations may be used. Further, clasps, inserts and clips, and hook and loops, are non-limiting examples of structures that may be used to form the connection between the headgear and the nasal interface.

The second or distal end 36 of each strap 32 may also be colored to stand out, such as for example, colored bright orange. The straps 32 may also include indicia to instruct an operator during installation of the device. For example, the straps 32 may include the word "PULL" and an arrow that points in the direction the straps 32 would be pulled to tighten the mask 14. The letters and arrows may be in black writing so that they are easily visible. Other suitable indicia may be used.

The head conforming portion 31 may be made from a variety of material. In one embodiment, the head-conforming portion 31 is a single piece of material that is foldable or collapsible, but rigid enough to assume the shape of a skull cap when unfolded and could be quickly placed onto the head of the person. Thus, the material, in this embodiment, may be resilient or form-holding such that it will readily take a shape suitable for placing onto the head of a person. A suitable form-holding material, such as for example plastic polymer or silicone, may be used for the head conforming portion 31.

Figure 5:
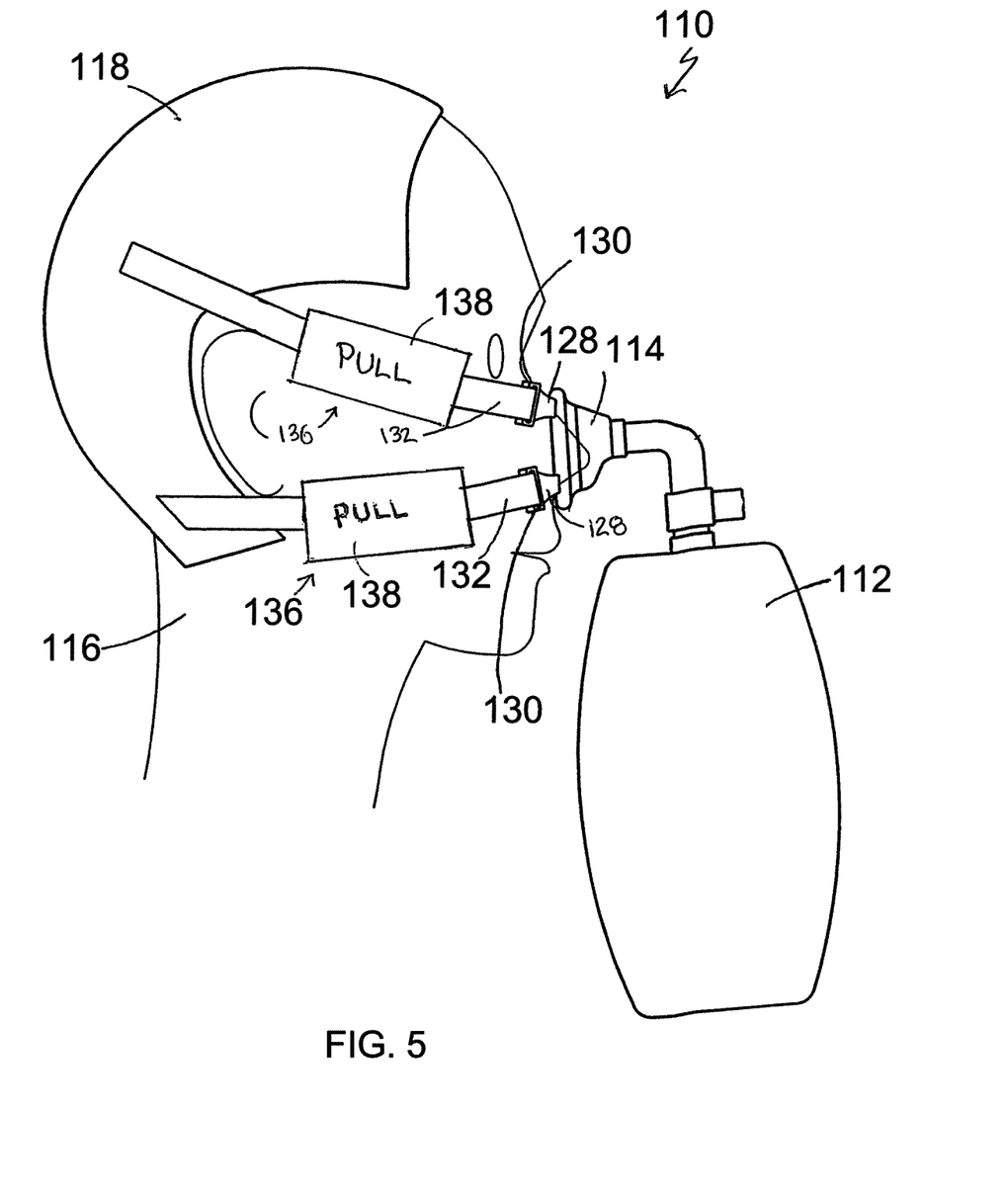
FIG. 5 is a side view of a second exemplary embodiment of a manual lung ventilation device arranged on a person.
Figure 7:
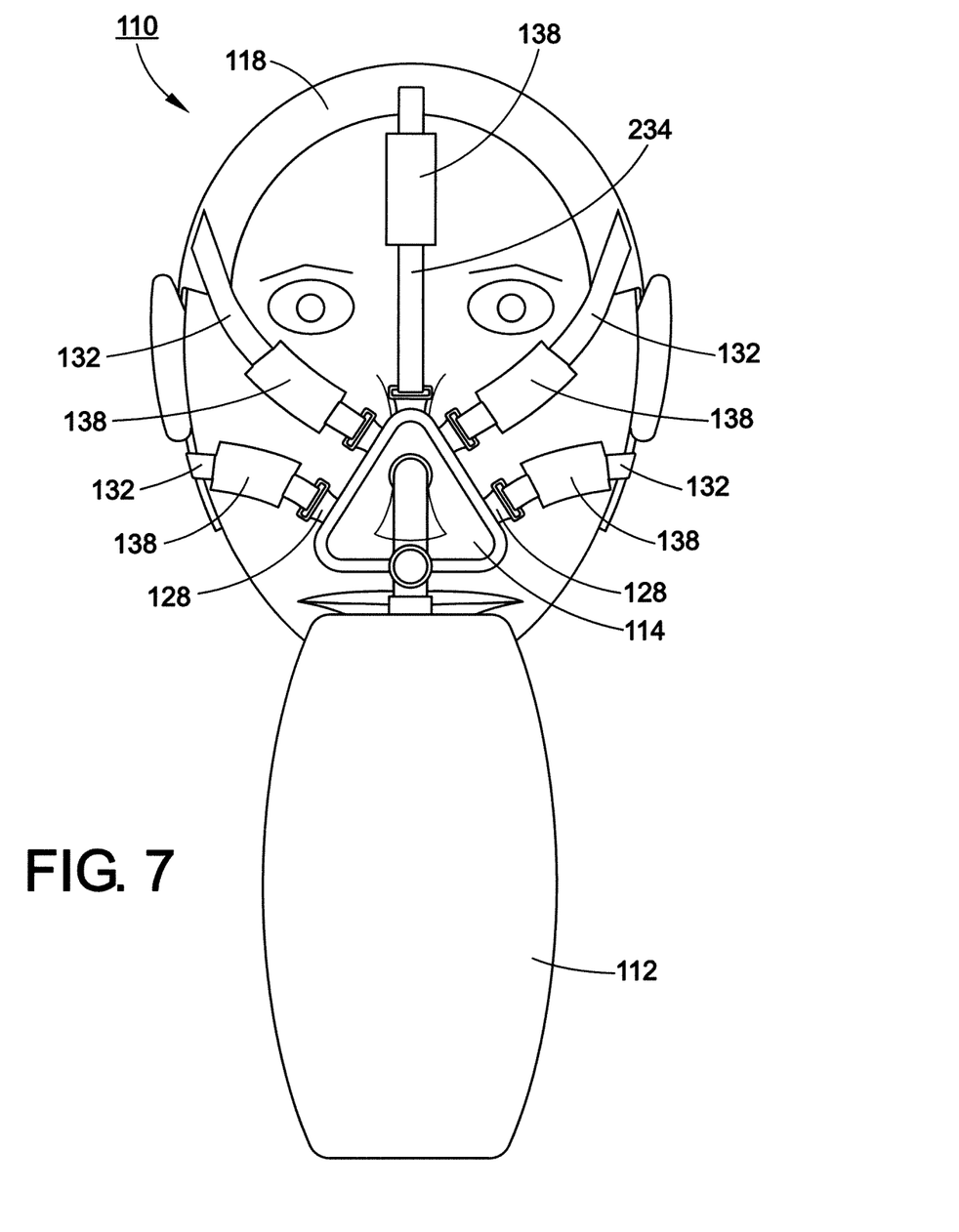
FIG. 7 is an alternate front view of the second exemplary embodiment of FIG. 5, showing a manual lung ventilation device with a center strap.

FIG. 5 and FIG. 7 illustrates a second exemplary embodiment of the manual lung ventilation device 110. The device 110 is similar to the device 10 of FIGS. 1-4 in that it includes a squeezable or flexible chamber or bag 112 in fluid communication with a nasal interface 114 having one or more attachment portions 128. The nasal interface 114 is adapted to be secured in place on the face of a person 116 by a headgear 118. One or more securing devices 132, 234 such as straps for example, attach the headgear 118 to the attachment portions 128 on the nasal interface 114. A single center strap 234 between the headgear 118 and the nasal interface 114 is utilized. The center strap 234 extends generally between the eyes of a person when the device is in position. The center strap 234 further stabilizes and secures the nasal interface 214 on the person's face. Compressing or squeezing the chamber 112 forces air through the nasal interface 114 and into the nasal passages of a person 116 to inflate and ventilate the person's lungs.

In the depicted embodiment, the one or more securing devices 132, 234 are realized as straps. The straps 132, 234 have a second or distal end 136 that includes an enlarged portion or tab that can be easily grasped between a person's thumb and forefinger. The enlarged portion 138 may be sized such that it does not fit through an opening 130 of the attachment portion 128. The enlarged portion 138 may be configured as part of the straps 132, 234. For example, the end of the straps 132, 234 may fold over upon itself and attach, clip, or otherwise be fixed in place such that the thickness of the end of the strap doubles in size. The enlarged portion 138, however, may also be a separate part that attaches to the distal end 136 of the strap 132, 234 by any suitable means. Thus, the mask 114 and the headgear 118 may be normally attached and not separable. In this manner, when the headgear 118 is placed on the person 116, the mask 114 is substantially positioned on the person's nose and the installer need only tighten the straps 132, 234 for the device 110 to be ready to be used. The enlarged portions 138, the attachment portions 128, or some other portion of the device 110, however, may be removable or adapted in some other way to allow the mask 114 to be detached from the headgear 118.

Figure 6:
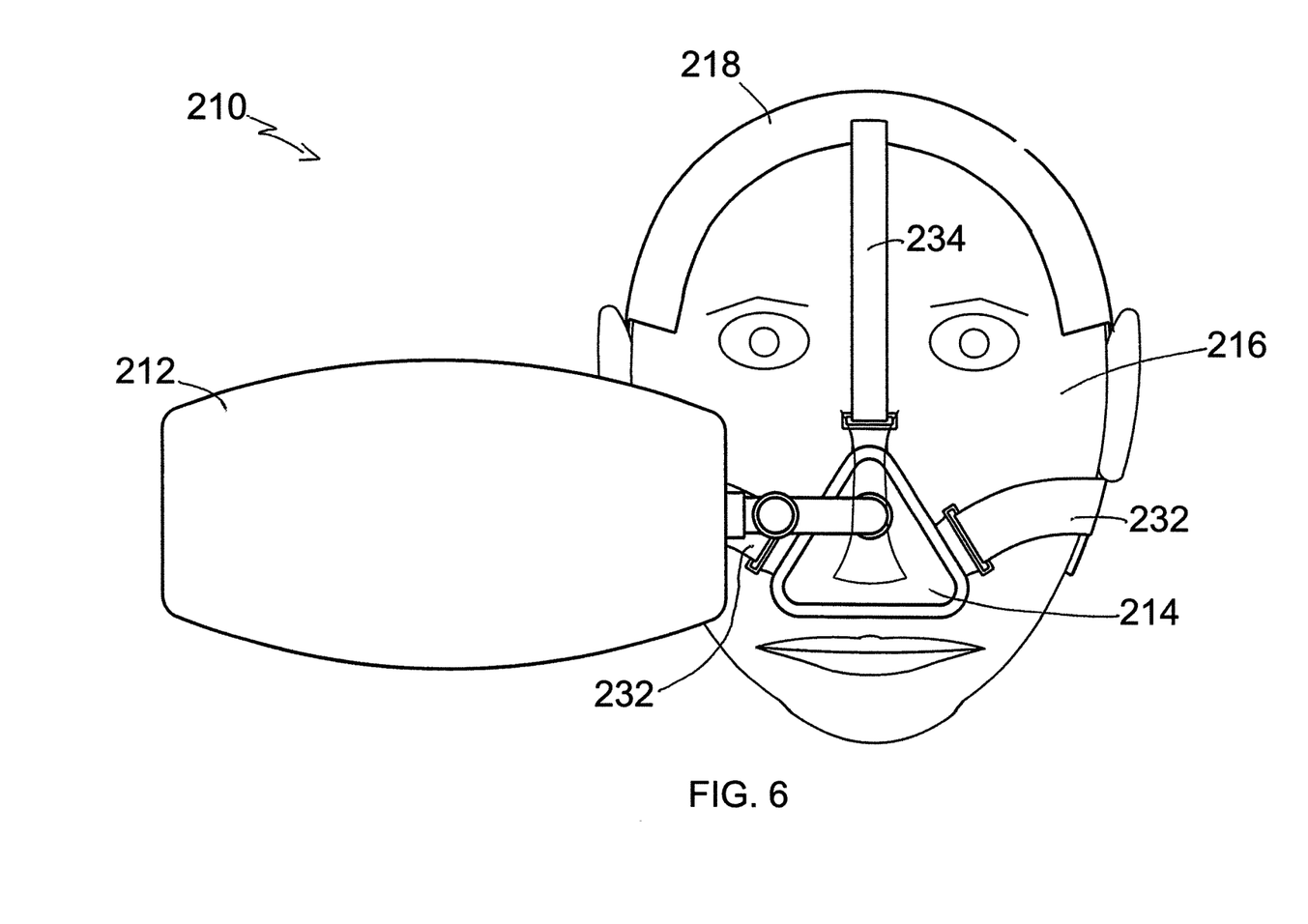
FIG. 6 is a front view of a third exemplary embodiment of a manual lung ventilation device arranged on a person.

FIG. 6 illustrates a third exemplary embodiment of a ventilation device 210 for resuscitation and lung ventilation. The device 210 is similar to the device 10 of FIGS. 1-4 in that it includes a squeezable or flexible chamber or bag 212 in fluid communication with a nasal interface 214. The nasal interface 214 is adapted to be secured in place on the face of a person 216 by a headgear 218. One or more securing devices 232 attach the headgear 218 to the nasal interface 214. Compressing or squeezing the chamber 212 forces air through the nasal interface 214 and into the nasal passages of a person 216 to inflate and ventilate the person's lungs.

The securing devices 232 on the headgear 218 and the nasal interface 214, however, differ from the securing devices 32 in the depicted embodiment of FIGS. 1-4. In the device 10, four straps 32 are illustrated, two on each side of the person's face. In the device 210, a single, thicker strap 232 is utilized on either side of the person's face and a single center strap or connection 234 between the headgear 218 and the nasal interface 214 is utilized. The center strap 234 extends generally between the eyes of a person when the device is in position. The center strap 234 further stabilizes and secures the nasal interface 214 on the person's face. As with the securing devices 32, the number, arrangement and configuration of the securing devices 232 may vary.

Thus, this application discloses a device and method suitable for successful acute manual respiratory resuscitation and/or lung ventilation. The device may include semi-rigid or stiff headgear to facilitate ease of proper placement on the head and an attachment between the headgear, nasal interface, conduit portion, and flexible chamber that allows the device to fall into proper position over the nose of the person with the placement of the headgear.

The invention has been described with reference to the preferred embodiments. Modification and alterations will occur to others upon a reading and understanding of this specification. It is intended to include all such modifications and alterations insofar as they come within the scope of the appended claims or the equivalents thereof.

The invention claimed is:
1. A manual lung ventilation device for ventilating the lungs of a person, comprising:
 a nasal interface configured to provide a fluid tight seal with the nasal passage of the person when the device is installed on the person, the nasal interface including a plurality of attachment portions, each attachment portion having an opening;

a flexible chamber in fluid communication with the nasal interface, wherein compressing the flexible chamber forces air through the nasal interface;

a skull cap having a head conforming portion made from a single piece of a form-holding material that is foldable, but rigid enough to assume a shape adapted to generally conform to the head of the person when unfolded; and a plurality of straps for connecting the nasal interface to the skull cap, each strap extending from a first end fixably attached to the skull cap through the opening of an attachment portion on the nasal interface to a distal end, the distal end having a fastener and including an enlarged portion that does not fit through the opening of the attachment portion, so that the nasal interface and the skull cap are not separable from each other, wherein the fastener secures the distal end to the strap or the head conforming portion, wherein the fastener is a hook or loop fastener, and wherein the strap or the head conforming portion includes a portion that is complementary to the fastener on the distal end.

2. The manual lung ventilation device of claim 1 wherein the plurality of straps includes a center strap that extends downward from a center of the skull cap to the nasal interface.

3. The manual lung ventilation device of claim 1 wherein the flexible chamber comprises a self-inflating bag.

4. The manual lung ventilation device of claim 1, wherein installing the skull cap onto the person automatically positions the flexible chamber in a desirable location for one-handed operation of the device.

5. The manual lung ventilation device of claim 1, wherein the skull cap is configured to conform to the person's head such that the nasal interface is positioned to fluidly communicate with the nasal passages of the person and the flexible chamber is positioned in a desirable location for one-handed operation of the device.

6. The manual lung ventilation device of claim 1, wherein the flexible chamber extends vertically downward from the nasal interface.

7. The manual lung ventilation device of claim 1, wherein the flexible chamber extends perpendicular from the nasal interface.

8. The manual lung ventilation device of claim 1, wherein the device is configured as a manually operated resuscitation device that does not require a mechanical source of positive airway pressure.

9. The manual lung ventilation device of claim 1, wherein the device is configured for one handed operation such that an operator of the device does not need to seal the nasal interface when the nasal interface and skull cap are installed on a person's head.

10. The manual lung ventilation device of claim 1, wherein the nasal interface, the flexible chamber, and the skull cap are not separable and form a single physical and functional unit.

11. The manual lung ventilation device of claim 1, wherein the distal end folds over upon itself and is fixed in place when the distal end is passed through the opening, and the distal end is subsequently unfolded to enlarge in size.

12. The manual lung ventilation device of claim 1, wherein the enlarged portion is a separate part that is attached to the distal end to enlarge the size of the distal end.

13. A manually operated resuscitation device for ventilating the lungs of a person, comprising:

a nasal mask;

a self-inflating bag in fluid communication with the nasal mask, wherein compression of the bag forces air from the bag through the nasal mask; and a skull cap having a head conforming portion made from a single piece of a form-holding material that is foldable, but rigid enough to assume a shape that conforms to the head of a person when unfolded;

the skull cap being connected to the nasal mask by a securing device comprising a plurality of straps;

wherein the nasal mask, the self-inflating bag, the skull cap, and the securing device are linked as a single unit in which the self-inflating bag is proximate to and carried by the nasal mask;

wherein the nasal mask, securing device, and skull cap are arranged to surround a volume for receiving the person's head, with the nasal mask being located at an opposite side of the volume from the skull cap; and wherein each of the plurality of straps extends from a first end that is fixably attached to the skull cap through a respective attachment portion on the nasal mask to a second end, the second end including an enlarged portion that does not fit through the respective attachment portion, so that the second end doubles in size.

14. The manually operated resuscitation device of claim 13 wherein the plurality of straps is adapted to hold the nasal mask in position when the nasal mask and the skull cap are installed on a person's head to permit one handed operation of the device.

15. The manually operated resuscitation device of claim 13 wherein the plurality of straps comprises a strap that generally extends downward from the skull cap to the nasal mask.

16. The resuscitation device of claim 13, wherein the self-inflating bag extends vertically downward from the nasal mask.

17. The resuscitation device of claim 13, wherein the self-inflating bag extends perpendicular from the nasal mask.

18. The manual lung ventilation device of claim 13, wherein the distal end folds over upon itself and is fixed in place when the distal end is passed through the opening, and the distal end is subsequently unfolded to enlarge in size.

19. The manual lung ventilation device of claim 13, wherein the enlarged portion is a separate part that is attached to the distal end to enlarge the size of the distal end.

20. A manual lung ventilation device for ventilating the lungs of a person, comprising:

a nasal mask configured to provide an air tight seal with the nasal passage of a person when the device is installed on the person, the nasal mask including a plurality of attachment portions, each attachment portion having an opening;

a flexible bag in fluid communication with the nasal mask through a conduit, wherein compressing the flexible bag forces air through the nasal mask;

a skull cap having a head conforming portion made from a single piece of a form-holding material that is foldable, but rigid enough to assume a shape adapted to generally conform to the head of the person when unfolded, wherein the form-holding material is a plastic polymer or silicone; and a plurality of straps, each strap extending from a first end that is fixably attached to the skull cap through a respective attachment portion on the nasal mask to a second end, the second end including an enlarged portion which is unfolded so that the thickness of the second end doubles in size and the second end does not fit through the respective attachment portion.

21. A method for accomplishing manual respiratory resuscitation and for ventilating the lungs of a person, comprising:
  receiving a manual ventilation device, the device comprising:
    a skull cap having a head conforming portion made from a single piece of a form-holding material that is foldable, but rigid enough to assume a shape adapted to generally conform to the head of the person when unfolded;
    a nasal interface; and
    a plurality of straps, each strap having a first end fixably attached to the skull cap and a distal end, each strap passing through an opening of an attachment portion of the nasal interface to connect the nasal interface to the skull cap and folding back toward the skull cap, the distal end being enlarged such that the distal end does not fit through the opening of the attachment portion, so that the skull cap and the nasal interface are not separable, and the distal end having a fastener that secures the distal end to the strap or the head conforming portion, wherein the fastener is a hook or loop fastener, and wherein the strap or the head conforming portion includes a portion that is complementary to the fastener on the distal end;
  placing the skull cap upon the head of the person;
  positioning the nasal interface over the nose of the person;
  securing the device by pulling the straps towards the skull cap and then fastening the distal end of each strap to the respective complementary portion on the strap or the head conforming portion; and
  compressing a flexible chamber attached to the nasal interface to deliver air from the chamber to the nasal interface to ventilate the person's lungs.

22. The method of claim 21 wherein the plurality of straps includes a center strap that generally extends downward from the skull cap to the nasal interface.

23. The method of claim 21, wherein the skull cap is configured to conform to the person's head such that the nasal interface is positioned to fluidly communicate with the nasal passages of the person and the flexible chamber is positioned in a desirable location for one-handed operation of the device.

* * * * *